United States Patent
Gosling (12)

(10) Patent No.: US 6,172,274 B1
(45) Date of Patent: Jan. 9, 2001

(54) SOLID CATALYST ALKYLATION PROCESS USING A WETTING ZONE

(75) Inventor: Christopher D. Gosling, Roselle, IL (US)

(73) Assignee: UOP LLC, Des Plaines, IL (US)

( * ) Notice: Under 35 U.S.C. 154(b), the term of this patent shall be extended for 0 days.

(21) Appl. No.: 09/212,907

(22) Filed: Dec. 16, 1998

(51) Int. Cl.$^7$ ................................. C07C 2/64; C07C 2/58
(52) U.S. Cl. ..................... 585/446; 585/467; 585/468; 585/709; 585/721; 585/722
(58) Field of Search .................... 385/446, 467, 385/468, 709, 721, 722

(56) References Cited

U.S. PATENT DOCUMENTS

| | | | |
|---|---|---|---|
| 3,851,004 | * 11/1974 | Yang | 585/467 |
| 5,157,196 | * 10/1992 | Crossland et al. | 585/720 |
| 5,190,904 | * 3/1993 | Crossland et al. | 502/85 |
| 5,292,981 | * 3/1994 | Huang et al. | 585/722 |
| 5,346,676 | * 9/1994 | Crossland et al. | 422/211 |
| 5,489,732 | 2/1996 | Zhang et al. | 585/467 |
| 5,672,798 | * 9/1997 | Zhang et al. | 585/467 |
| 5,675,048 | * 10/1997 | Zhang et al. | 585/467 |
| 5,744,681 | * 4/1998 | Joly et al. | 585/709 |

OTHER PUBLICATIONS

Ralph D. Nelson, Jr. "Handling Powders (Dispersion)" in: *Kirk–Othmer Encyclopedia of Chemical Technology*, (New York, John Wiley and Sons, Inc., 1996) pp. 1093–1113, vol. 19 4$^{th}$ Ed.—TP.E685 1992 ISBN 0–471–52688–6 (v.19).

G.D. Parfitt and H.A. Barns "The Dispersion of Fine Particles in Liquid Media" in: *Mixing in the Process Industries*, (Boston, Butterworth–Heinemann Ltd., 1992), pp. 99–117 2$^{nd}$ Ed.,—ISBN 0 7506 11103.

*Perry's Chemical Engineers Handbook*, edited by D.W. Green, (New York, McGraw–Hill Book Company, 1984) pp. 19–24, 6$^{th}$ Ed.—TP151.P45.

\* cited by examiner

Primary Examiner—Walter D. Griffin
(74) Attorney, Agent, or Firm—John G. Tolomei; John F. Spears, Jr.; Michael A. Moore

(57) ABSTRACT

A solid catalyst alkylation process that wets catalyst particles with the alkylation substrate prior to introducing the catalyst particles to a liquid phase alkylation reactor is disclosed. A vapor stream from the wetting step that comprises the alkylation substrate and a reactor effluent stream comprising product alkylate and excess alkylation substrate are both passed to the product recovery zone, which recovers the alkylate product and recycles the alkylation substrate. Routing the vapor stream and the reactor effluent stream together to the product recovery zone minimizes pressure imbalances, ensures steady catalyst flow, and minimizes equipment costs. This process is applicable to alkylation processes that produce motor fuels.

19 Claims, 1 Drawing Sheet

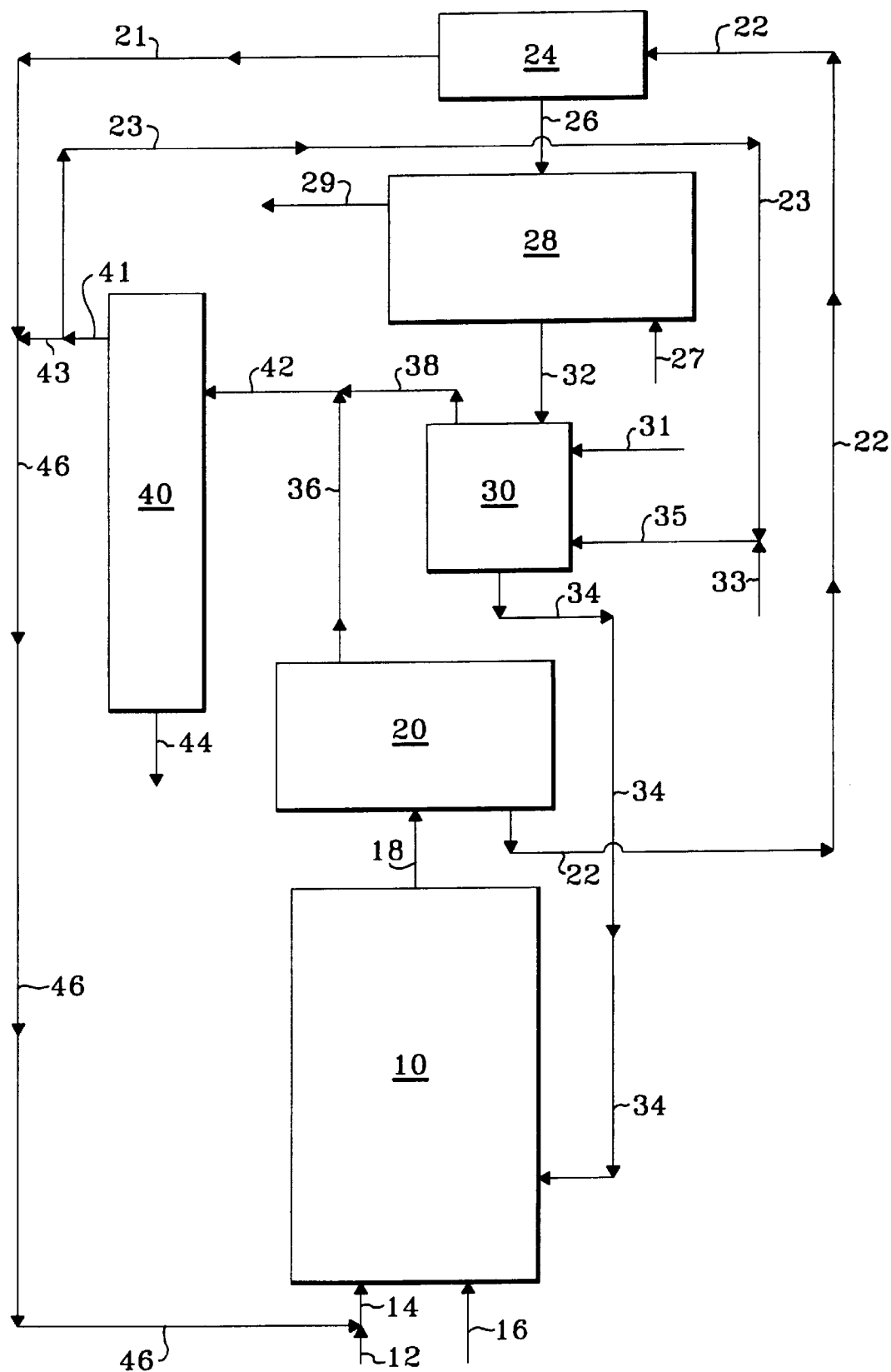

SOLID CATALYST ALKYLATION PROCESS USING A WETTING ZONE

FIELD OF THE INVENTION

This invention relates to the alkylation of hydrocarbons such as aromatics and paraffins to produce useful chemicals and motor fuel. This invention specifically relates to a method for wetting solid catalyst particles in an alkylation process.

BACKGROUND OF THE INVENTION

Hydrocarbon alkylation is widely used in the petroleum refining and petrochemical industries to produce a variety of useful acyclic and cyclic hydrocarbon products which are consumed in motor fuel, plastics, detergent precursors, and petrochemical feedstocks. Much of the installed base of alkylation capacity uses liquid phase hydrofluoric acid, generally referred to as HF, as the catalyst. The use of HF in these applications has a long record of highly dependable and safe operation. However, the potential damage from an unintentional release of any sizable quantity of HF and the need to safely dispose of some byproducts produced in the process has led to an increasing demand for alkylation process technology which does not employ liquid phase HF as the catalyst.

Numerous solid alkylation catalysts have been described in the open literature. However, these catalysts appear to suffer from unacceptably high deactivation rates when employed at commercially feasible conditions. While some catalysts have a sufficiently useful lifetime to allow the performance of alkylation, the rapid change in activity results in a change in product composition and also requires the periodic regeneration of the catalyst with the accompanying removal of the reaction zone from operation. It is very desirable to provide a continuous process for alkylation which is not subjected to periodic reaction zone stoppages or variation in the product stream composition.

In hydrocarbon processing, continuous catalytic processes commonly use transport reactors. In a transport reactor, the catalyst bed as a whole moves and is transported with a fluid phase. Thus, a transport reactor can be contrasted with a fixed bed catalytic reactor and with an ebulliated bed catalytic reactor. In a fixed bed reactor the catalyst particles do not move, and in an ebulliated bed reactor the catalyst particles are suspended in a fluid but the settling velocity of the catalyst particles balances the fluid upflow velocity so that the catalyst bed as a whole is not transported with the fluid phase. Although it is generally the case that the direction of catalyst flow through a transport reactor is upward, the direction may also be downward, horizontal, a direction that is intermediate between vertical and horizontal, or a combination of these directions.

When the direction of catalyst flow through a transport reactor is upward, the transport reactor is often called a riser-reactor. Riser-reactors are commonly used in hydrocarbon processing, such as fluidized catalytic cracking and more recently in motor fuel alkylation. In a common arrangement, a fluid hydrocarbon reactant engages a solid hydrocarbon conversion catalyst at the bottom of a riser-reactor and transports the catalyst in a fluidized state up the riser-reactor. During the ascent through the riserreactor, the catalyst promotes certain desired conversion reactions among the reactants in order to produce desired products. A stream of catalyst and hydrocarbon products, byproducts, and unreacted reactants if any discharges from the top of the riser-reactor into a separation zone. The hydrocarbons and the catalyst disengage in the separation zone, with the hydrocarbons being withdrawn overhead for recovery and the catalyst dropping by gravity to the bottom of the separation zone. Despite some deactivation that may have occurred to the catalyst in the riser-reactor, some of the catalyst that collects at the bottom of the separation zone may have enough residual activity that it can be reused in the riser-reactor without first being withdrawn from the separation zone for regeneration. Such still active catalyst is recirculated through a recirculation conduit from the bottom of the separation zone to the bottom of the riser-reactor, where the catalyst contacts reactants again.

Most commercial alkylation catalysts, however, require periodic regeneration of the catalyst with the accompanying removal of the catalyst from the reaction zone for regeneration. Depending on the particular catalyst and on the nature and degree of the deactivation, the periodic catalyst regeneration may be in the liquid phase or in the vapor phase. Liquid phase or "mild" regeneration comprises contacting the catalyst with a liquid phase hydrocarbon, which is commonly a feed hydrocarbon, such as isobutane, with dissolved hydrogen. Vapor phase or "severe" regeneration, on the other hand, comprises contacting the catalyst with hydrogen gas at a higher temperature and/or for a longer time than liquid phase regeneration. Vapor phase regeneration, which is also called "hydrogen stripping," is a more intense regeneration than liquid phase regeneration. Whereas liquid phase regeneration helps to remove alkylate, light byproducts, and lightly sorbed contaminants from the catalyst, vapor phase regeneration helps to remove more strongly sorbed species, such as heavies which, if allowed to accumulate on the catalyst, would deactivate the catalyst and would cause the alkylate yield to decline. As used herein, the collective term "heavies" refers to oligomers having twelve or more carbon atoms. Because liquid phase regeneration may not remove these strongly sorbed oligomers, vapor phase regeneration is usually performed after a specified number, such as three or four, of liquid phase regenerations. But, in processes where the rate of catalyst deactivation or rate of yield loss is extremely rapid, vapor phase regenerations may be done either after each liquid phase regeneration or even instead of liquid phase regeneration. Thus, vapor phase regeneration can be a critical step in a continuous alkylation process, regardless of whether the alkylation process includes liquid phase regeneration.

In contrast to regeneration in the vapor phase, the alkylation reactor generally operates in at least partially liquid phase conditions, including supercritical conditions. Consequently, catalyst particles that are withdrawn from the alkylation reactor for regeneration contain entrained liquid hydrocarbons, both in the pores of the catalyst particles and in the interstitial volume between the catalyst particles. Although in theory this entrained hydrocarbon liquid could remain with the catalyst particles and be removed along with the strongly sorbed species during vapor phase regeneration, it is preferred as a practical matter to remove these liquid hydrocarbons prior to vapor phase regeneration in order to simplify the handling of the vapors that are employed in vapor phase regeneration and to exclude the need for separating liquids from the vapor phase regeneration gases. Thus, prior to vapor phase regeneration, the entrained liquid is removed from the catalyst in a process that is known as dewetting.

Subsequent to vapor phase regeneration, the catalyst particles must, of course, ultimately be returned to the alkylation reactor. But adding the vapor phase regenerated catalyst directly to the alkylation reactor, however, creates several problems. These same problems also arise when adding dry fresh catalyst as makeup directly to the alkylation reactor. In either case, directly contacting the catalyst with liquid hydrocarbons generates the heat of adsorption of the liquid hydrocarbons on the catalyst particles. If not removed from the alkylation reactor, this heat can cause side reactions that produce undesirable byproducts. Moreover, the released heat can vaporize hydrocarbons that are preferably maintained as liquids, not vapors, at alkylation conditions. Thus, the released heat necessitates the use of extra equipment to cool, condense, and recycle the vaporized hydrocarbons. In addition, the vaporization of hydrocarbons can cause pressure imbalances in vessels through which catalyst particles flow that can stop or reverse the direction of catalyst flow between the vessels.

Thus, a method is sought for wetting vapor phase regenerated or fresh catalyst particles with liquid hydrocarbons in a manner that does not cause undesirable side reactions, that does not require the use of additional condensers and other equipment for recycling hydrocarbon vapors, and that does not impede catalyst flow.

SUMMARY OF THE INVENTION

This invention is a process for alkylating an alkylation substrate with an alkylating agent that uses a particularly economical and effective method of wetting catalyst particles which are being introduced into an alkylation reactor which operates at least partially in the liquid phase. Prior to being added to the alkylation reactor, the catalyst particles are wetted with the alkylation substrate in a wetting zone. A vapor stream that is recovered from the wetting zone passes to the same recovery facilities that recover the product alkylate from other hydrocarbons in the alkylation reactor effluent. Routing the vapor stream to the product recovery facilities not only minimizes the equipment for recovery of any vaporized alkylation substrate from the wetting zone but in some embodiments also helps to balance the pressures of the wetting zone and the alkylation reactor, thereby ensuring steady catalyst flow from the wetting zone to the alkylation reactor. In addition, any vaporization of the liquid alkylation substrate in the wetting zone as a result of the wetting helps to remove the heat of adsorption that is generated by wetting the catalyst.

Thus, a primary objective of this invention is to provide a process for the alkylation of an alkylation substrate with an alkylating agent in the presence of a solid catalyst. A second objective of this invention is to provide a liquid phase alkylation process that uses solid catalyst particles and which minimizes the amount of necessary equipment. A third objective of this invention is to provide an alkylation process that introduces solid catalyst particles into a liquid phase alkylation reactor in a manner that avoids problems arising from the release of the heat of adsorption in the alkylation reactor.

Accordingly, in a broad embodiment, this invention is a process for the alkylation of an alkylation substrate with an alkylating agent. An alkylating agent and a first substrate stream comprising an alkylation substrate pass to a reaction zone. In the reaction zone, the alkylating agent alkylates the alkylation substrate to produce alkylate. The reaction occurs in the presence of catalyst particles having a first weight ratio of alkylation substrate per dry catalyst particles and at alkylation conditions that include at least a partial liquid phase. A reaction zone effluent stream comprising alkylate is withdrawn from the reaction zone. Catalyst particles having a second weight ratio of alkylation substrate per dry catalyst particles that is less than the first weight ratio pass to a wetting zone. A second substrate stream comprising the alkylation substrate also passes to the wetting zone. The first substrate stream or the second substrate stream comprises at least a portion of a recycle stream. In the wetting zone, alkylation substrate contacts catalyst particles having the second weight ratio at wetting conditions. The wetting conditions are sufficient to maintain at least a portion of the alkylation substrate that contacts the catalyst particles in a liquid phase. A wetting zone vapor stream comprising the alkylation substrate in the vapor phase is withdrawn from the wetting zone. Catalyst particles having a third weight ratio of alkylation substrate per dry catalyst particles that is greater than the second weight ratio are also withdrawn from the wetting zone. Catalyst particles having the third weight ratio and withdrawn from the wetting zone pass to the reaction zone. At least a portion of the wetting zone vapor stream and at least a portion of the reaction zone effluent stream pass to a product recovery zone. A product stream comprising alkylate and the recycle stream comprising the alkylation substrate are withdrawn from the product recovery zone. The product stream is recovered from the process.

In another embodiment, this invention is a process for the alkylation of an alkylation substrate with an alkylating agent. An alkylating agent and a first substrate stream comprising an alkylation substrate pass to a reaction zone. In the reaction zone, the alkylating agent alkylates the alkylation substrate to produce alkylate. The reaction occurs in the presence of catalyst particles having a first weight ratio of alkylation substrate per dry catalyst particles at alkylation conditions. The alkylation conditions include at least a partial liquid phase. Catalyst particles having a second weight ratio of alkylation substrate per dry catalyst particles that is not greater than the first weight ratio are withdrawn from the reaction zone. A reaction zone effluent stream comprising alkylate is also withdrawn from the reaction zone. Catalyst particles having the second weight ratio and withdrawn from the reaction zone pass to a dewetting zone. In the dewetting zone, at least a portion of the alkylation substrate is removed from the catalyst particles. Catalyst particles having a third weight ratio of alkylation substrate per dry catalyst particles that is less than the first weight ratio are withdrawn from the dewetting zone. A second substrate stream comprising the alkylation substrate passes to a wetting zone along with catalyst particles having the third weight ratio and withdrawn from the dewetting zone. The first substrate stream or the second substrate stream comprises at least a portion of a recycle stream. In the wetting zone, alkylation substrate contacts catalyst particles having the third weight ratio at wetting conditions. The wetting conditions are sufficient to maintain at least a portion of the alkylation substrate that contacts the catalyst particles in a liquid phase. A wetting zone vapor stream comprising the alkylation substrate in the vapor phase is withdrawn from the wetting zone. Catalyst particles having a fourth weight ratio of alkylation substrate per dry catalyst particles that is greater than the third weight ratio are also withdrawn from the wetting zone. Catalyst particles having the fourth weight ratio and which were withdrawn from the wetting zone pass to the reaction zone. At least a portion of the wetting zone vapor stream and at least a portion of the reaction zone effluent stream pass to a product recovery zone. A product stream comprising alkylate and the recycle stream comprising the alkylation substrate are withdrawn from the product recovery zone. The product stream is recovered from the process.

Other embodiments, purposes, and objectives will become clear from the ensuing description.

INFORMATION DISCLOSURE

U.S. Pat. No. 5,489,732 (Zhang et al.) discloses an alkylation process that uses a solid catalyst which is regenerated by a "mild," low-temperature, liquid phase washing and by a "severe," hot vapor phase hydrogen stripping operation.

The teachings of U.S. Pat. No. 5,489,732 are incorporated herein by reference.

The dispersion of powders in liquids, including wetting the powder in to the liquid, is discussed in the article entitled "Handling Powders (Dispersion)," written by Ralph D. Nelson, Jr., starting on page 1093 in Volume 19 of Kirk-Othmer *Encyclopedia of Chemical Technology*, Fourth Edition, edited by Jacqueline I. Kroschwitz, published by John Wiley and Sons, Inc., New York, in 1996, and also in Chapter 6 entitled "The Dispersion of Fine Particles in Liquid Media," written by G. D. Parfitt and H. A. Barnes, starting on page 99 in *Mixing in the Process Industries*, Second Edition, edited by N. Hamby et al., published by Butterworth-Heinemann Ltd., Boston, in 1992.

Cooling by evaporating solvent during mixing of pastes and viscous materials is mentioned on page 19-24 of *Perry's Chemical Engineers' Handbook*, Sixth Edition, edited by R. H. Perry and D. W. Green, published by McGraw-Hill Book Company, New York, in 1984.

BRIEF DESCRIPTION OF THE DRAWING

The drawing is a process flow diagram of an embodiment of the invention.

DETAILED DESCRIPTION OF THE INVENTION

The alkylation substrate for this invention may be essentially any hydrocarbon which is retained as an easily flowable liquid phase material and which may be alkylated via solid catalyst at the conditions employed in the alkylation reactor. The alkylation substrate may be an aromatic hydrocarbon, if the objective is to produce such chemicals as ethylbenzene and cumene or to produce linear alkyl benzenes which are sulfonated to detergents. Although benzene is the principal aromatic of interest, aromatics such as alkyl-substituted benzenes, condensed ring systems generally, and alkylated derivatives thereof may be used. Examples of such aromatics are toluene, ethylbenzene, propylbenzene, and so forth; xylene, mesitylene, methylethylbenzene, and so on; naphthalene, anthracene, phenanthrene, methyinaphthalene, dimethyinaphthalene, and tetralin. More than one aromatic can be used. If, on the other hand, the objective is to produce motor fuels, then the alkylation substrate may be a paraffinic hydrocarbon, such as a branched paraffin having from 4 to 6 carbon atoms. Suitable paraffinic hydrocarbons are illustrated by 2-methylpropane (commonly called isobutane), 2-methylbutane (or isopentane), 2,3-dimethylbutane, 2-methylpentane, and 3-methylpentane.

The alkylation substrate is alkylated with an alkylating agent. If the objective is to produce chemicals such as ethylbenzene or cumene or to produce motor fuels, then the alkylating agent is typically an olefinic hydrocarbon containing from 2 to about 6 carbon atoms. Examples of such olefins include ethylene, propylene, 1-butene, cis-2-butene, trans-2-butene, and iso-butene. However, if the objective is to produce linear alkyl benzenes, then the alkylating agent can be an olefinic hydrocarbon having from about 2 to about 20 carbon atoms, and usually from about 10 to about 15 carbon atoms. More than one olefin may be used. The alkylating agent may be chosen also from a variety of compounds other than olefins including monohydric alcohols. Suitable alcohols include ethanol and methanol. For instance, methanol is widely described in the literature as being useful in the methylation of benzene and toluene.

The subject process can be performed using any solid, that is, heterogeneous, catalyst which is stable and has the required activity and selectivity for the desired reaction at the conditions needed to maintain liquid phase reactants in the alkylation reactor. A large number of catalysts have been proposed for the production of motor fuel by alkylation including nonzeolitic catalysts and various zeolitic catalysts. Suitable nonzeolitic catalysts include sulfated zirconia and tungstated zirconia. Among suitable zeolitic catalysts, U.S. Pat. No. 4,384,161, for example, describes the use of a large pore zeolite and a Lewis acid. The zeolites referred to include ZSM-4, ZSM-3, the faujasites including zeolite Y, and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. The use of these Lewis acids is not preferred in the subject process as they provide their own waste handling and safety problems. They also will probably require provisions for the circulation of the Lewis acid, which may complicate the process as shown by the teaching of the just cited U.S. Pat. No. 4,935,577. U.S. Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art heterogeneous paraffin alkylation catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Analogs of these catalysts without the metal cations are described in U.S. Pat. Nos. 2,999,074 and 3,318,820 which describe preparation techniques which can be applied to the preferred catalysts. The preferred refractory oxide is alumina having a surface area greater than 50 $m^2/g$, but the use of other oxides including titania, zirconia, silica, boria, and aluminum phosphate is contemplated. The preferred catalyst also contains a metal component active for olefin hydrogenation deposited on the inorganic oxide prior to reaction of the bound surface hydroxyl groups with the metal halides. This metal may be chosen from the group consisting of nickel, platinum, palladium, and ruthenium with the first three of these metals being preferred. The catalyst contains one or more monovalent metal or alkaline earth metal cations selected from the group consisting of lithium, sodium, potassium, cesium, silver, copper, beryllium, magnesium, calcium, and barium. Subsequent to the deposition of these metals and the controlled calcination of the composite, the composite is reacted with a Friedel-Crafts metal halide. The metal may be aluminum, zirconium, tin, tantalum, gallium, antimony, or boron. Suitable halides are the fluorides, chlorides, and bromides.

The presence of a highly active metal hydrogenation component on the catalyst will promote hydrogenation of the substrate olefin if both the olefin and hydrogen simultaneously contact the catalyst. This potential waste of the olefin and hydrogen can be avoided by careful design and operation of the process to avoid having both the olefin and hydrogen in simultaneous contact with the catalyst. This can be done by flushing the hydrogen or olefin from the catalyst before inserting it into a zone containing the other compound as described above.

Silicalites have been described as useful alkylation catalysts for the production of monoalkylbenzenes in U.S. Pat. No. 4,489,214 (J. R. Butler et al.) and as useful in methylating toluene to produce paraxylene in U.S. Pat. No. 4,444,989 (F. E. Herkes). The use of ZSM-5 zeolites in aromatic alkylation is described in U.S. Pat. No. 3,751,506. ZSM-5 zeolites that have been treated with one or more compounds or elements to improve their selectivity for paraselective alkylation of aromatic hydrocarbons are. described in U.S. Pat. No. 4,420,418. The use of zeolite L, zeolite omega, and zeolite beta as alkylation catalysts for the selective alkylation of benzene is described in U.S. Pat. No. 4,301,316. The use of a number of natural and synthetic zeolites including clinoptilolite and zeolite Y as alkylation catalysts is described in U.S. Pat. No. 3,251,897.

The catalyst may be in the form of any suitable shape and size that results in a solid catalyst which flows readily in both dry and wet states and which is readily fluidized at the moderate liquid flow rates employed in a transport reactor such as a riser-reactor. The catalyst can therefore be present as small irregular particles or as uniformly shaped particles. It is preferred that the catalyst is present as "microspheres" having an average diameter of from about 0.1 to about 2.0 mm and more preferably less than about 1.0 mm.

The term "wetting" as used herein refers to the formation of a liquid-solid interface in place of a gas-solid interface. In a wetting zone of the present invention, solid catalyst particles are wetted into a liquid comprising the alkylation substrate. Generally, the catalyst particles that enter the wetting zone have a weight ratio of alkylation substrate per dry catalyst particles that is less than the weight ratio of alkylation substrate per dry catalyst particles in the zone, such as the alkylation reactor or the alkylation reactor effluent separation zone, into which catalyst particles that leave the wetting zone pass. As used herein, the weight of dry catalyst particles is the weight of the catalyst particles on a volatile free basis, where the volatiles are determined by heating the catalyst particles to 900° C. (1652° F.). The weight ratio of aromatic substrate per dry catalyst particles that enter the wetting zone is generally from about 1:1000 to about 1:1 00.

Weight ratios of the aromatic substrate per dry catalyst particles of less than about 1:100 for the catalyst particles entering the wetting zone indicate that the pores of the catalyst particles are relatively dry in the sense that the pores at least partially contain a gas rather than the alkylation substrate. The particular gas that occupies the pores of the catalyst particles entering the wetting zone depends on the source of the entering catalyst particles and is not, therefore, an essential element of the present invention. The gas preferably has certain preferred characteristics, however. First, the gas should be capable of being displaced from the pores of the catalyst by the alkylation substrate. For example, when catalyst with gas sorbed within the pores is introduced on or under the surface of a reservoir or an accumulation of the alkylation substrate, the alkylation substrate effectively displaces, or desorbs, from the pores a substantial portion of the gas. By displacing a substantial portion of the gas it is meant that generally at least 50% but more typically at least 90% of the gas present within the pores is displaced from the pores of the catalyst. Second, the gas should not cause any undesired physical or chemical transformation of the catalyst. For example, the gas should not oxidize the catalytic metal if a reduced metal is desired, and the gas should not reduce the metal if an oxidized metal is desired. Third, the gas should be capable of being readily mixed with and separated from the alkylation substrate and the alkylate. Thus, where the alkylation substrate and the alkylate contain carbon and hydrogen, the gas is preferably not oxygen, which would produce a combustible or explosive mixture.

The catalyst particles that enter the wetting zone may originate from several possible sources. For example, fresh catalyst particles, which are being added as make-up to the alkylation process in order to compensate for catalyst particles that are lost or withdrawn from the process, may enter the wetting zone. Because fresh catalyst particles are often packaged and shipped under an inert atmosphere in order to preserve the select properties of the catalyst, the pores of the catalyst particles may thus contain an inert gas such as nitrogen. In another example, the entering catalyst particles may comprise catalyst that has been withdrawn from a hereinafter described dewetting zone, such as regenerated catalyst that has been used for alkylation reactions and has subsequently undergone vapor phase regeneration. Vapor phase or "severe" regeneration typically comprises contacting the catalyst with hydrogen gas at an elevated temperature and/or for an extended period of time. Vapor phase regeneration, which is also called "hydrogen stripping," is a more intense regeneration than liquid phase or "mild" regeneration in that vapor phase regeneration helps to remove strongly sorbed species, such as the previously mentioned heavies, which if allowed to accumulate on the catalyst would deactivate the catalyst and would cause the alkylate yield to decline. Thus, the gas in the pores of the catalyst particles that enter the wetting zone may be hydrogen. Instead of, or in addition to, nitrogen or hydrogen, other gases may be present in the pores of the entering catalyst particles. Such other gases include light paraffins such as methane, ethane, propane; other inert gases such as helium, neon, or argon; and other noncombustible gases such as carbon dioxide. The pores of the catalyst particles that enter the wetting zone may even contain the alkylation substrate, which may result if the "severe" regeneration step comprises contacting the catalyst with a mixed vapor-liquid stream, such as a mixture of hydrogen and the alkylation substrate, rather than a vapor-only stream. However, if the pores of the catalyst particles entering the wetting zone do contain alkylation substrate because of this or any other reason, it is nevertheless a requirement of this invention that the entering catalyst particles have a weight ratio of substrate per dry catalyst particles that is less than the weight ratio of substrate per dry catalyst particles in the zone into which the catalyst particles leaving the wetting zone pass.

The wetting zone may comprise any suitable container for contacting the entering catalyst particles with the alkylation substrate. In its simplest form, the wetting zone comprises a vessel that defines a space for containing a reservoir of the liquid alkylation substrate, and a disengaging space above the liquid reservoir for disengaging the displaced gas from the liquid alkylation substrate. Although internals such as baffles, impactors, and screens within the wetting zone vessel are not necessary, such baffles and screens may be helpful for disengaging the displaced gas, which may form bubbles in the liquid or a stable froth on the surface of the liquid. Such phase separation devices are conventional and are within the knowledge of a person of ordinary skill in the art of liquid-gas phase separation. See, for example, pages 18-70 to 18-88 of *Perry's Chemical Engineers' Handbook*, Sixth Edition, edited by R. H. Perry and D. W. Green, published by McGraw-Hill Book Company, New York, in 1984.

The wetting zone typically operates at a temperature of from about 40 to about 150° F. (4 to 66° C.) and a pressure of from about 200 to about 600 psi(g) (1379 to 4137 kPa(g). Generally, the wetting zone temperature is within about 10° F. (5.6° C.) of the boiling point of the alkylation substrate at the wetting zone pressure. Some of the difference between the wetting zone temperature and the substrate boiling point is due at least in part to the presence of solid catalyst particles, gas, and other liquid components in the liquid phase of the wetting zone. These substances can suppress or elevate the boiling point of the liquid phase mixture relative to that of the alkylation substrate.

A vapor stream is withdrawn from the wetting zone, typically at a location sufficiently above the top surface of the liquid alkylation substrate so as to minimize any entrainment of liquid in the exiting vapor stream. The vapor stream that is withdrawn from the wetting zone typically comprises gas displaced from the pores of the catalyst particles, as well as alkylation substrate vapor. The concentration and the amount of alkylation substrate in the vapor stream depends on many factors that influence the operating conditions of the wetting zone, including the weight ratio of alkylation substrate per dry catalyst particles, the flow rate, and the temperature of the catalyst particles entering the wetting zone; the heat of adsorption of the alkylation substrate on the catalyst particles; the heat of vaporization of the alkylation substrate; the temperature of any make-up alkylation substrate to the wetting zone; and the loss or removal of any heat, such as by indirect heat exchange, from the wetting zone. Typically, the heat of adsorption of the alkylation substrate on the catalyst particles is at least 50% of the heat of vaporization of the alkylation substrate. Generally, the vapor stream will be saturated with the alkylation substrate because the temperature of the wetting zone is close to the boiling point of the alkylation substrate. The vapor stream that is withdrawn from the wetting zone passes to product recovery facilities which are described hereinafter. However, a portion of the vaporized alkylation substrate may be passed to a condenser located either inside or outside of the wetting zone, condensed, and recycled as liquid alkylation substrate to the wetting zone.

In addition to the vapor stream, solid catalyst particles wetted with the alkylation substrate are also withdrawn from the wetting zone. As a result of the wetting that occurs in the wetting zone, the catalyst particles leaving the wetting zone have a weight ratio of alkylation substrate per dry catalyst particles that is more than the weight ratio of alkylation substrate per dry catalyst particles entering the wetting zone. Because the preferred range of weight ratios of alkylation substrate per dry catalyst particles for the leaving catalyst particles depends on many factors including the nature of the catalyst particles and the alkylation substrate, it is helpful to describe the preferred range of weight ratios of alkylation substrate per dry catalyst particles in qualitative rather than quantitative terms. For purposes of this qualitative description, the following definitions are helpful. "Bound alkylation substrate" in the catalyst particles is that alkylation substrate which exerts a vapor pressure less than that of the pure alkylation substrate liquid at the given temperature. Alkylation substrate liquid may become bound by retention in small capillaries, by homogeneous solution throughout the catalyst particles, and by chemical sorption, known as chemisorption, on surfaces of the solid particles. The process by which the alkylation substrate becomes bound generates at least some heat of adsorption of the alkylation substrate and the catalyst particles. On the other hand, "unbound alkylation substrate" in the catalyst particles includes that alkylation substrate which exerts a vapor pressure equal to that of the pure alkylation substrate liquid at the given temperature. Unbound alkylation substrate liquid may become retained in large pores of the catalyst particles, and by physical sorption on the catalyst particles, but it is not sorbed chemically, that is, it is not chemisorbed, on the catalyst particles. Because the unbound alkylation substrate is not chemisorbed on the catalyst particles, the sorption, if any, of unbound alkylation substrate on the catalyst particles does not generate any heat of adsorption. Finally, "free alkylation substrate" is alkylation substrate that is not in the pores of the catalyst particles, but rather is alkylation substrate that is between the pores or is in the interstitial or void volume between the catalyst particles. Like unbound alkylation substrate, free alkylation substrate is not chemisorbed on the catalyst particles and the introduction of free alkylation substrate to a bed of particles does not generate any heat of adsorption.

Thus, the weight ratio of alkylation substrate per dry catalyst particles of the catalyst particles leaving the wetting zone is generally such that there is at least some bound alkylation substrate on the catalyst particles. To the extent that some bound alkylation substrate is present with the catalyst particles leaving the wetting zone, the heat of adsorption that is generated when the catalyst particles pass to the alkylation reactor or the separation zone is minimized. Accordingly, the heat that must be removed from the reactor or the separation zone is minimized. More preferably, the weight ratio of alkylation substrate per dry catalyst particles is such that there is at least some unbound alkylation substrate on the catalyst particles. Even more preferably, the weight ratio of alkylation substrate per dry catalyst particles is such that there is at least some free alkylation substrate with the catalyst particles leaving the wetting zone. Generally, as the amount of free alkylation substrate with the exiting catalyst particles increases, the outlet stream of the wetting zone tends to become more of a slurry, and so, rather than agglomerating in clumps, the catalyst particles tend to flow freely. The weight ratio of alkylation substrate per dry catalyst particles for the particles leaving the wetting zone is generally less than, but may be the same as or more than, the weight ratio of alkylation substrate per dry catalyst particles in the reactor or separation zone. Typically, the weight ratio of alkylation substrate per dry catalyst particles for the particles leaving the wetting zone is more than 1:2.

The catalyst particles withdrawn from the wetting zone usually enter a zone in which the catalyst particles have a weight ratio of alkylation substrate per dry catalyst particles that is more than the weight ratio of alkylation substrate per dry catalyst particles of the catalyst particles entering the wetting zones. This means that the zone into which the catalyst particles from the wetting zone pass generally operates at least partially in a liquid phase, and can be the alkylation reactor, or the separation zone that separates the alkylation reactor effluent, or both. Other than the weight ratio of alkylation substrate per dry catalyst particles, the operating conditions of the alkylation reactor and the separation zone are not critical to the present invention. Thus, the alkylation reactor can be any suitable reactor for reacting an alkylation substrate and an alkylating agent in the presence of a solid catalyst, and the separation zone can be any suitable separator for separating the alkylation reactor effluent into a stream comprising liquid and vapor components and a stream comprising the solid catalyst. U.S. Pat. No. 5,489,732 (Zhang et al.) discloses alkylation reactors and separation zones and their corresponding operating conditions that are suitable for this invention.

The stream that comprises the liquid and vapor components separated from the alkylation reactor effluent is passed to product recovery facilities which are conventional and need not, therefore, be described in detail herein. In brief, the product recovery facilities reject from the process components that are lighter than the alkylation substrate and/or components that are lighter than the alkylating agent, recycle to the alkylation reactor any unreacted alkylation substrate and/or alkylating agent, and recover the alkylate as product. In a process for the alkylation of isobutane with butenes, the product recovery facilities typically comprise a distillation column called an isostripper and another column called a depropanizer. The isostripper separates the entering liquids and vapors into an overhead stream comprising isobutane and lighter components, a sidecut stream comprising normal butanes which is rejected from the process, and a bottom stream comprising alkylate which is recovered as product. The overhead stream passes to the depropanizer, which rejects propane and lighter components and produces a stream comprising isobutane which is recycled to the alkylation reactor.

The catalyst particles that are separated from the alkylation reactor effluent may be passed to any suitable destination, and, in this invention's broadest terms, the destination is not a critical invention of the present invention. In other words, in this invention's broadest sense, there is no requirement that any of the catalyst particles that are separated from the alkylation reactor effluent be recycled to the wetting zone. However, in applying this invention to an alkylation process, it is within the scope of this invention that some of the catalyst particles withdrawn from the alkylation reactor are recycled to the wetting zone.

When the catalyst particles separated from the reactor effluent are recycled to the wetting zone, the catalyst particles are first passed to a zone, such as a drying zone or a vapor phase regeneration zone, where the weight ratio of alkylation substrate per dry catalyst particles of the catalyst particles is reduced to less than that in the zone into which the catalyst particles that exit the wetting zone pass. All that is required is that, prior to being reintroduced to the wetting zone, the weight ratio of the stream containing the catalyst particles is decreased somewhat compared to the weight ratio of the zone into which the catalyst particles are passed. This zone, in the most general terms, is called a dewetting zone. For general methods and equipment for drying solids, see, for example, pages 20-1 to 20-74 of Perry's Chemical Engineers' Handbook, Sixth Edition, edited by R. H. Perry and D. W. Green, published by McGraw-Hill Book Company, New York, in 1984.

Prior to being passed to a dewetting zone, such as a drying zone or a vapor phase regeneration zone as described in the previous paragraph, the catalyst particles separated from the reactor effluent may undergo liquid phase regeneration. Liquid phase, or "mild" regeneration typically comprises contacting the catalyst particles with liquid alkylation substrate containing dissolved hydrogen for an extended period of time and at a temperature that is lower than that for vapor phase regeneration. Liquid phase regeneration helps to remove alkylate, light byproducts, and lightly sorbed contaminants from the catalyst particles.

The FIGURE represents a preferred embodiment of the invention. The following description of the FIGURE is with respect to the alkylation of isobutane with mixed butene isomers, but this description is not intended to limit the scope of the invention as set forth in the claims. A liquid feed stream containing isobutane enters the process through a line 12 and combines with a liquid recycle stream also containing isobutane flowing through a line 46, and a combined stream of feed and recycle isobutane flows through a line 14 to the alkylation reactor 10. Another feed stream containing butene isomers enters the process through a line 16 and flows to the alkylation reactor 10. Catalyst particles enter the alkylation reactor 10 through a line 34. Within the alkylation reactor 10, isobutane, which is present in a molar excess relative to the butene isomers, reacts with the butene isomers to produce $C_8$ alkylate. Oligomeric byproducts having more than eight carbon atoms also form, including heavies which deposit on the catalyst particles. The reaction takes place in the presence of the catalyst particles and at least partially in the liquid phase.

An alkylation reactor effluent stream containing liquid alkylate, excess liquid isobutane, and catalyst particles flows through a line 18 and enters a separation zone 20, which is a quiescent zone where the catalyst particles disengage from the liquid hydrocarbons. A separator effluent stream comprising alkylate and isobutane flows through a line 36, and a spent catalyst stream comprising catalyst particles with the heavy oligomeric deposits and isobutane liquid flows through a line 22 to a drying zone 24. Although in theory the isobutane liquid could remain with the catalyst particles and be removed along with the heavy oligomeric deposits during vapor phase regeneration, the isobutane liquid is preferably removed prior to vapor phase regeneration in order to minimize the complexity of handling liquids in what would, except for the heavy oligomers, be a liquid-free, vapor phase regeneration process. Drying zone 24 removes some of the isobutane from the entering catalyst particles as isobutane vapor, which may be condensed by means not shown in the FIGURE and which is recycled to the alkylation reactor 10 through a line 21, a line 46, and the line 14. After drying, catalyst particles flow from drying zone 24 through a line 26 to a vapor phase regeneration zone 28. In vapor phase regeneration zone 28, hot hydrogen gas enters through a line 27 and contacts and regenerates the catalyst particles by removing the heavy oligomers from the surface of the catalyst particles. Means that are not shown in the FIGURE separate the heavy oligomers from the hydrogen, and the heavy oligomers leave the process through a line 29.

Regenerated catalyst particles flow to a wetting zone 30 through a line 32. Line 32 may include a means such as a valve, which is not shown in the FIGURE, for allowing catalyst particle flow and for restricting gas flow between the vapor phase regeneration zone 28 and the wetting zone 30. By such means the vapor phase regeneration zone 28 can operate at a pressure that is different from that of the wetting zone 30 and that of the separation zone 20. The pressure of the vapor phase regeneration zone 28 is generally at least 5 psi (34.5 kPa), and preferably from 5 to 15 psi (34.5 to 103.4 kPa), greater than the pressure of the wetting zone 30. Because of the means for restricting gas flow in the line 32, fluctuations in the pressure of the vapor phase regeneration zone 28 generally do not propagate to the wetting zone 30 or to the separation zone 20. Therefore, pressure fluctuations in the wetting zone 30 or the separation zone 20 are minimized.

In the wetting zone 30, the entering catalyst particles are contacted with liquid isobutane. Some of the liquid isobutane in the wetting zone 30 is recycled via lines 23 and 35 from the product recovery facilities 40 as described hereinafter, and the remainder is makeup isobutane that enters through lines 33 and 35. Fresh catalyst particles, which have nitrogen in their pores, may be added as makeup to the wetting zone 30 via a line 31. Wetted catalyst particles and isobutane are withdrawn from the wetting zone 30 through a line 34 and are recycled to the alkylation reactor 10. The weight ratio of isobutane per dry catalyst particles of the wetted catalyst particles in the line 34 is more than 1:2.

The wetting by the liquid isobutane displaces hydrogen from the pores of the regenerated catalyst particles and nitrogen from the pores of the fresh catalyst particles, if any. The wetting generates a heat of adsorption, which vaporizes a portion of the liquid isobutane in the wetting zone 30. A vapor stream comprising hydrogen and vaporized isobutane flows from the wetting zone 30 through a line 38, and combines with the previously-mentioned separator effluent stream in the line 36. The combined stream thus contains alkylate and hydrogen, and in addition isobutane from both the separation zone 20 and the wetting zone 30. The combined stream flows through a line 42 to product recovery facilities 40, which recover the alkylate in a line 44 and which comprise means not shown in the FIGURE to condense at least a portion of the isobutane. Isobutane liquid recycles to the alkylation reactor 10 through lines 41, 43, 46, and 14. Some of the liquid isobutane 40 from the product recovery facilities is recycled to the wetting zone 30 also, via lines 41, 23, and 35. It is expected, however, that the flow of recycle isobutane in the line 41 will generally exceed the requirement for the flow of isobutane to the wetting zone 30, and hence some isobutane in the line 41 will flow to the alkylation reactor 10. Means for recovering hydrogen from product recovery facilities 40, and for recycling the recovered hydrogen to vapor phase regeneration zone 28 are not shown in the FIGURE.

In a particularly preferred variation on the embodiment shown in the FIGURE, the line 18 is eliminated, and the alkylation reactor 10 and the separator 20 are contained within a common vessel, which is referred to herein as a reaction-separator. One example of such an arrangement is shown in FIG. 1 of the previously-mentioned U.S. Pat. No. 5,489,732, which employs a riser-reactor within a vessel which contains the separation zone and which also receives regenerated catalyst from a vapor phase regeneration zone. Such an arrangement can minimize the difference in pressure between the separator and the point at which the line 34 discharges wetted catalyst into the reactor-separator. In addition, in this particularly preferred variation the differences in pressure across the lines 36 and 38 are minimized. Thus, with these three pressure differences minimized, the wetting zone 30 operates at substantially the same pressure as the point at which the wetted catalyst particles enter the reactor-separator. In other words, the pressure of the wetting zone 30 is balanced with that of the reactor-separator. Accordingly, if the wetting zone 30 is located above the reactor-separator, catalyst particles can flow from the wetting zone 30 to the reactor-separator through the line 34 by gravity flow. Most importantly, however, the balancing of the pressures helps ensure that the pressure in the reactor-separator does not exceed the pressure in the wetting zone 30 to the extent that the flow of catalyst particles through the line 34 is stopped or, worse, reversed. A reversal of catalyst particle flow can result in unsatisfactory operations. This invention helps to prevent fluctuations in the pressure difference between the reactor-separator pressure and the wetting pressure from exceeding 50% of the average pressure difference between the reactor-separator pressure and the wetting pressure.

Numerous other variations on the flow scheme in the FIGURE are possible and are within the scope of the invention. First, rather than combining the wetting zone vapor stream in the line 38 with the separator effluent stream in the line 36 to form the combined stream in the line 42, the streams in the lines 38 and 36 could each be routed separately to product recovery facilities 40 and the line 42 could be eliminated. In this variation, if the product recovery facilities 40 comprise a distillation column, and lines 36 and 38 are routed to the same distillation column, then preferably line 38 is routed to an upper portion of the column and line 36 is routed to a portion of the column below the upper portion. If lines 38 and 36 are separately routed to the product recovery facilities 40, the possibilities arise that the pressure drops through the two separate lines will not be equal and/or that the pressures at each line's destination in product recovery facilities 40 may not be the same. Consequently, the previously-described balancing of the pressures between, on the one hand, the wetting zone 30 and, on the other hand, the alkylation reactor 10 may be lost. Therefore, this first variation might require additional instrumentation for measuring the pressures in the wetting zone 30 and the alkylation reactor 10 and for controlling the desired pressure difference between the two.

Two other variations on the flow scheme in the FIGURE involve the routing of the flow of catalyst particles between the catalyst-containing zones in the FIGURE. In the first of these two variations, some or all of the catalyst particles leaving the wetting zone 30 can flow to the separation zone 20 rather than to the alkylation reactor 10. The separation zone 20 can be a separate vessel or can be combined with the alkylation reactor 10 in a common vessel, as described previously. If all of the catalyst particles from the wetting zone 30 flows to the separation zone 20, then at least a portion of the catalyst particles from the separation zone 20 would flow to the alkylation reactor 10, instead of all the catalyst particles from the separation zone 20 flowing to the drying zone 24, as shown in the FIGURE. In a second variation involving the flow of the catalyst particles, some or all of the catalyst particles flowing in the line 22 can pass to a liquid phase or "mild" regeneration zone. In this variation, a portion of the catalyst particles that is withdrawn from the liquid phase regeneration zone may be passed directly to the alkylation reactor 10, with the remainder passing to the drying zone 24.

Transport of the catalyst particles from one catalyst-containing zone to another can be done by a variety of means, such as gravity flow, pneumatic lifting using a gas or a vapor for fluidizing and lifting, hydraulic lifting using a liquid for fluidizing and lifting, and mechanical conveying using buckets, belts, or other devices. One possible orientation of the zones in the FIGURE would be to locate the separation zone 20, the drying zone 24, the vapor phase regeneration zone 28, and the wetting zone 30 above the alkylation reactor 10. In this orientation, transporting the catalyst particles would comprise, first, hydraulic lifting upward in a riser in the alkylation reactor 10 to the separation zone 20; then, gravity flow downward from the separation zone 20 followed by hydraulic lifting upward using liquid isobutane in a lift line to the drying zone 24; and, finally, gravity flow from the drying zone 24, through the vapor phase regeneration zone 28, through the wetting zone 30, and ultimately to the alkylation reactor 10. Another possible orientation would be to place the separation zone 20 and the wetting zone 30 above the alkylation reactor 10 and to locate the drying zone 24 and the vapor phase regeneration zone 28 below the alkylation reactor 10. In this alternate orientation, transporting the catalyst particles would comprise, first, hydraulic lifting upward in a riser in the alkylation reactor 10 to the separation zone 20; then, gravity flow downward from the separation zone 20 through the drying zone 24 and the vapor phase regeneration zone 28; then, pneumatic lifting upward using hydrogen or isobutane vapor in a lift line to the wetting zone 30; and, finally, gravity flow from the wetting zone 24 to the alkylation reactor 10. Other orientations are also possible, and the orientation of these catalyst-containing zones is not an essential element of this invention.

What is claimed is:

1. A process for the alkylation of an alkylation substrate with an alkylating agent, the process comprising the steps of:
   a) passing an alkylating agent and a first substrate stream comprising an alkylation substrate to a reaction zone, alkylating the alkylation substrate with the alkylating agent in the reaction zone to produce alkylate in the presence of catalyst particles having a first weight ratio of alkylation substrate per dry catalyst particles at alkylation conditions comprising at least a partial liquid phase, and withdrawing from the reaction zone a reaction zone effluent stream comprising alkylate;
   b) passing catalyst particles having a second weight ratio of alkylation substrate per dry catalyst particles that is less than the first weight ratio and a second substrate stream comprising the alkylation substrate to a wetting zone, wherein the first substrate stream or the second substrate stream comprises at least a portion of a recycle stream, contacting catalyst particles having the second weight ratio in the wetting zone with alkylation substrate at wetting conditions, the wetting conditions being sufficient to maintain at least a portion of the alkylation substrate that contacts the catalyst particles in a liquid phase, withdrawing from the wetting zone a wetting zone vapor stream comprising the alkylation substrate in the vapor phase, wherein a portion of the alkylation substrate that contacts the catalyst particles in the wetting zone forms the alkylation substrate in the wetting zone vapor stream, and withdrawing from the wetting zone catalyst particles having a third weight ratio of alkylation substrate per dry catalyst particles that is greater than the second weight ratio;
   c) passing catalyst particles having the third weight ratio and withdrawn from the wetting zone to the reaction zone; and
   d) passing at least a portion of the wetting zone vapor stream and at least a portion of the reaction zone effluent stream to a product recovery zone, and withdrawing from the product recovery zone a product stream comprising alkylate that is recovered from the process and the recycle stream comprising the alkylation substrate.

2. A process for the alkylation of an alkylation substrate with an alkylating agent, the process comprising the steps of:
   a) passing an alkylating agent and a first substrate stream comprising an alkylation substrate to a reaction zone, alkylating the alkylation substrate with the alkylating agent in the reaction zone to produce alkylate in the presence of catalyst particles having a first weight ratio of alkylation substrate per dry catalyst particles at alkylation conditions comprising at least a partial liquid phase, and withdrawing from the reaction zone catalyst particles having a second weight ratio of alkylation substrate per dry catalyst particles that is not greater than the first weight ratio and a reaction zone effluent stream comprising alkylate;
   b) passing catalyst particles having the second weight ratio and withdrawn from the reaction zone to a dewetting zone, removing at least a portion of the alkylation substrate from catalyst particles in the dewetting zone, and withdrawing from the dewetting zone catalyst particles having a third weight ratio of alkylation substrate per dry catalyst particles that is less than the first weight ratio;
   c) passing a second substrate stream comprising the alkylation substrate and catalyst particles having the third weight ratio and withdrawn from the dewetting zone to a wetting zone, wherein the first substrate stream or the second substrate stream comprises at least a portion of a recycle stream, contacting catalyst particles having the third weight ratio with the alkylation substrate in the wetting zone at wetting conditions, the wetting conditions being sufficient to maintain at least a portion of the alkylation substrate that contacts the catalyst particles in a liquid phase, withdrawing from the wetting zone a wetting zone vapor stream comprising the alkylation substrate in the vapor phase, wherein a portion of the alkylation substrate that contacts the catalyst particles in the wetting zone forms the alkylation substrate in the wetting zone vapor stream, and withdrawing from the wetting zone catalyst particles having a fourth weight ratio of alkylation substrate per dry catalyst particles that is greater than the third weight ratio;
   d) passing catalyst particles having the fourth weight ratio and withdrawn from the wetting zone to the reaction zone;
   e) passing at least a portion of the wetting zone vapor stream and at least a portion of the reaction zone effluent stream to a product recovery zone, and withdrawing from the product recovery zone a product stream comprising alkylate that is recovered from the process and the recycle stream comprising the alkylation substrate.

3. The process of claim 2 wherein the alkylation substrate is isobutane.

4. The process of claim 2 wherein the catalyst particles comprise a refractory inorganic oxide impregnated with a monovalent cation.

5. The process of claim 2 further characterized in that the wetting conditions comprise a pressure of from about 200 to about 600 psi(g) and a temperature of from about 40 to about 150° F.

6. The process of claim 5 further characterized in that the temperature is within about 10° F. of the boiling point of the alkylation substrate at the pressure.

7. The process of claim 2 further characterized in that the reaction zone comprises an alkylation reactor and a separation zone, the alkylating agent and the first substrate stream are passed to the alkylation reactor, the alkylation substrate is alkylated with the alkylating agent in the alkylation reactor, a reactor effluent stream comprising the alkylate and catalyst particles is withdrawn from the alkylation reactor, the reactor effluent stream is passed to the separation zone, the reactor effluent stream is separated in the separation zone, and the catalyst particles withdrawn from the reaction zone and the reaction zone effluent stream are withdrawn from the separation zone.

8. The process of claim 2 further characterized in that the dewetting zone comprises a drying zone and a vapor phase regeneration zone, the catalyst particles withdrawn from the reaction zone have heavies sorbed thereon, the catalyst particles withdrawn from the reaction zone pass to the drying zone, at least a portion of the isobutane is removed from catalyst particles in the drying zone, catalyst particles after having isobutane removed are passed to the vapor phase regeneration zone, and at least a portion of the heavies is removed from catalyst particles in the vapor phase regeneration zone to produce the catalyst particles withdrawn from the dewetting zone.

9. The process of claim 2 further characterized in that catalyst particles in the dewetting zone are contacted with hydrogen, the catalyst particles withdrawn from the dewetting zone have hydrogen sorbed thereon, the wetting conditions are sufficient to displace at least a portion of the hydrogen from the catalyst particles in the wetting zone, the wetting zone vapor stream comprises hydrogen, and a light stream comprising hydrogen is recovered from the product recovery zone.

10. The process of claim 2 wherein the third weight ratio is less than 1:100.

11. The process of claim 2 wherein the fourth weight ratio is more than 1:2.

12. The process of claim 2 further characterized in that the reaction zone operates at a reaction zone pressure, the wetting conditions comprise a wetting pressure, and the difference between the reaction zone pressure and the wetting pressure fluctuates by less than 50% of the average difference between the reaction zone pressure and the wetting pressure.

13. The process of claim 2 wherein the catalyst particles withdrawn from the reaction zone have alkylate sorbed thereon, and further characterized in that the passing of catalyst particles from the reaction zone to the dewetting zone comprises passing the catalyst particles to a liquid phase regeneration zone, removing at least a portion of the alkylate from catalyst particles in the liquid phase regeneration zone, withdrawing catalyst particles from the liquid phase regeneration zone, and passing catalyst particles from the liquid phase regeneration zone to the dewetting zone.

14. The process of claim 2 further characterized in that at least a portion of the alkylation substrate vaporized in the wetting zone passes to a condensing zone and is condensed in the condensing zone, and at least a portion of the alkylation substrate condensed in the condensing zone forms at least a portion of the second substrate stream.

15. The process of claim 2 further characterized in that the alkylation substrate has a heat of vaporization and the contacting of the catalyst particles in the wetting zone produces a heat of adsorption that is at least 50% of the heat of vaporization.

16. The process of claim 2 further characterized in that a portion of the second substrate stream combines with the catalyst particles withdrawn from the wetting zone to produce a combined stream and the combined stream passes to the reaction zone.

17. The process of claim 2 further characterized in that the fourth weight ratio is less than the first weight ratio.

18. The process of claim 2 further characterized in that the product recovery zone comprises a distillation column having an upper portion and a lower portion, the wetting zone vapor stream passes to the upper portion of the distillation column, and the reaction zone effluent stream passes to the lower portion.

19. A process for the alkylation of isobutane with butenes, the process comprising the steps of:

a) passing butenes, a first isobutane stream comprising isobutane, and at least a portion of a recycle stream to an alkylation reactor, alkylating isobutane with butenes in the alkylation reactor to produce alkylate in the presence of catalyst particles at alkylation conditions comprising at least a partial liquid phase, by-producing heavies in the alkylation reactor, and withdrawing a reactor effluent stream comprising isobutane, alkylate, and catalyst particles having heavies sorbed thereon from the alkylation reactor;

b) passing the reactor effluent stream to a separation zone, separating the reactor effluent stream in the separation zone, withdrawing from the separation zone catalyst particles having heavies sorbed thereon and having a weight ratio of isobutane per dry catalyst particles of more than 1:2, and withdrawing from the separation zone a separation effluent stream comprising isobutane and alkylate;

c) passing catalyst particles withdrawn from the reaction zone to a drying zone, removing isobutane from catalyst particles in the drying zone, and withdrawing catalyst particles from the drying zone;

d) passing catalyst particles withdrawn from the drying zone to a vapor phase regeneration zone, contacting catalyst particles with hydrogen and removing heavies from catalyst particles in the vapor phase regeneration zone, and withdrawing from the vapor phase regeneration zone catalyst particles having hydrogen sorbed thereon and having a weight ratio of isobutane per dry catalyst particles of less than 1:100;

e) passing a second isobutane stream comprising isobutane to a wetting zone, passing catalyst particles withdrawn from the vapor phase regeneration zone to the wetting zone, contacting catalyst particles with isobutane in the wetting zone at wetting conditions, the wetting conditions being sufficient to maintain at least a portion of isobutane that contacts the catalyst particles in a liquid phase and sufficient to displace hydrogen from catalyst particles in the wetting zone, withdrawing from the wetting zone a wetting zone vapor stream comprising hydrogen and isobutane vapor, wherein a portion of the isobutane that contacts the catalyst particles in the wetting zone forms the isobutane in the wetting zone vapor stream, and withdrawing from the wetting zone catalyst particles having a weight ratio of isobutane per dry catalyst particles that is greater than 1:2;

f) passing catalyst particles withdrawn from the wetting zone to the alkylation reactor; and g) combining the vapor stream and the separator effluent stream to form a combined stream, passing the combined stream to a product recovery zone, separating the combined stream in the product recovery zone, and withdrawing from the product recovery zone a product stream comprising the alkylate that is recovered from the process, the recycle stream comprising isobutane, and a light stream comprising hydrogen that is recovered from the process.

* * * * *